United States Patent [19]

Lee et al.

[11] Patent Number: 5,006,150
[45] Date of Patent: Apr. 9, 1991

[54] SUBSTITUTED HETEROCYCLOHEXANE-3,5-DIONES

[75] Inventors: Shy-Fuh Lee, Sunnyvale; Richard J. Anderson, Palo Alto; Gary W. Luehr, Sacramento; Carole R. Scott, Newark, all of Calif.

[73] Assignee: Sandoz Ltd., Basel, Switzerland

[21] Appl. No.: 530,487

[22] Filed: May 29, 1990

Related U.S. Application Data

[63] Continuation of Ser. No. 360,551, Jun. 1, 1989, abandoned, which is a continuation-in-part of Ser. No. 185,566, Apr. 25, 1988, abandoned, which is a continuation-in-part of Ser. No. 156,269, Feb. 12, 1988, abandoned, which is a continuation-in-part of Ser. No. 58,443, Jun. 5, 1987, abandoned.

[51] Int. Cl.$^5$ .................. A01N 43/00; C07D 309/10; C07D 309/22
[52] U.S. Cl. .......................................... 71/88; 549/417; 549/331; 549/28; 549/23; 546/220; 546/219; 546/16; 71/89; 71/90; 71/94
[58] Field of Search ............................ 549/417; 71/88

[56] References Cited

U.S. PATENT DOCUMENTS 4,695,673 9/1987 Heather et al. ..................... 568/310
4,728,745 3/1988 Carter et al. ........................ 549/417

Primary Examiner—Nicky Chan
Attorney, Agent, or Firm—Allen E. Norris

[57] ABSTRACT

Substituted benzoyl-2H-pyran-3,5-(4H,6H)-diones and related compounds, intermediates therefor, synthesis thereof, and the use of said diones for the control of weeds.

7 Claims, No Drawings

SUBSTITUTED HETEROCYCLOHEXANE-3,5-DIONES

This application is a continuation of application Ser. No. 360,551, filed on June 1, 1989, now abandoned, which is a continuation-in-part of application Ser. No. 185,566, filed Apr. 25, 1988, now abandoned, which is a continuation-in-part of application Ser. No. 156,269, filed on Feb. 12, 1988, now abandoned, which is a continuation-in-part of application Ser. No. 058,443, filed on June 5, 1987 and now abandoned.

This invention relates to novel substituted benzoyl-2H-pyran-3,5-(4H,6H)-diones and related compounds, intermediates therefor, synthesis thereof, and the use of said compounds for the control of weeds.

More particularly, the compounds of the present invention are represented by the following formula (I):

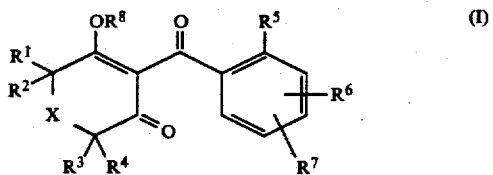

wherein,

X is oxygen, $S(0)_n$ or $NR^{11}$;

each of $R^1$, $R^2$, $R^3$ and $R^4$ is, independently, hydrogen, $C_{1-8}$alkyl or $COOR^9$, or $R^1$ and $R^2$ can together form a $C_{3-6}$alkylene;

$R^5$ is $C_{1-8}$alkyl, optionally substituted with one to six halogen atoms; alkoxy, optionally substituted with one to six halogen atoms; $S(0)_n R^{12}$; halogen; or nitro;

each of $R^6$ and $R^7$ is, independently, hydrogen; halogen; $C_{1-8}$alkyl, optionally substituted with one to six halogen atoms; $C_{1-8}$alkoxy, optionally substituted with one to six halogen atoms; $C_{1-8}$alkylcarbonyl; $C_{1-8}$alkoxycarbonyl; $NR^9R^{10}$; $SO_2NR^9R^{10}$; $S(0)_n R^{12}$; nitro; or cyano; with the proviso that neither of $R^6$ nor $R^7$ is attached to the 6 position;

$R^8$ is hydrogen, $C_{1-8}$alkyl, $C_{1-8}$alkylcarbonyl, $C_{1-8}$alkoxycarbonyl, benzoyl, $C(0)NR^9R^{10}$, $C_{1-8}$alkylsulfonyl, $P(0)-(OR^{11})_2$ or $R^9P(0)OR^{11}$;

each of $R^9$ and $R^{10}$ is, independently, hydrogen or $C_{1-8}$alkyl;

$R^{11}$ is $C_{1-8}$alkyl; and $R^{12}$ is $C_{1-8}$alkyl, optionally substituted with one to six halogen atoms;

each of n and n' is zero, one or two.

In the description and claims hereinafter, each of X, n, n' and $R^1$-$R^{12}$ is as defined above, unless otherwise specified.

In the practice of the present invention, X is preferably oxygen, sulfur or $NR^{11}$.

Where any of the substituents $R^1$-$R^7$ and $R^{12}$ is or comprises halogen, such halogen is conveniently selected from bromo, chloro and fluoro.

Where any of $R^1$-$R^7$ and $R^9$-$R^{12}$ is or comprises $C_{1-8}$alkyl, it is preferably of one to four carbons.

Where any of $R^5$-$R^8$ is or comprises $C_{1-8}$alkoxy, it is preferably of one to four carbons.

Each of $R^1$-$R^4$ is preferably hydrogen or $C_{1-4}$alkyl; such alkyl is more preferably of one to three carbons.

$R^5$ conveniently signifies $C_{1-4}$alkyl optionally substituted with halogen, $C_{1-4}$alkyl-$S(0)_n$, halogen or nitro; it is preferably methyl, $CF_3$, $C_{1-3}$alkylsulfonyl, chloro, bromo or nitro.

$R^6$ conveniently signifies hydrogen, $C_{1-4}$alkyl optionally substituted with halogen, $C_{1-4}$alkyl-$S(0)_n$, optionally substituted with halogen, $C_{1-4}$alkoxy optionally substituted with halogen, halogen or nitro; it is preferably hydrogen, $CF_3$, $C_{1-3}$alkylsulfonyl, chloro$C_{1-3}$alkylsulfonyl, methoxy, chloro, fluoro or nitro.

$R^6$ is preferably in the 4-position.

$R^7$ is preferably hydrogen.

$R^8$ is conveniently hydrogen, $C_{1-4}$alkyl, $C_{4-8}$alkyl. carbonyl, benzoyl or $C_{1-4}$alkylsulfonyl. It is preferably hydrogen, methyl, ethyl, t-butylcarbonyl, isobutylcarbonyl, benzoyl or methylsulfonyl.

Preferred subgroups of the present invention have one or more of the following features:

$R^1$ and $R^3$ are preferably $C_{1-4}$alkyl, more preferably $R^1$, $R^2$ and $R^3$ are $C_{1-4}$alkyl, most preferably $R^1$, $R^2$, $R^3$ and $R^4$ are $C_{1-4}$alkyl.

$R^5$ is nitro, methyl or methylsulfonyl.

$R^6$ is chloro and is in the 4position.

$R^7$ is hydrogen.

$R^8$ is hydrogen, methyl, $C_{4-8}$alkylcarbonyl or benzoyl.

Examples of especially preferred substituent meanings are

For $R^1$, $R^2$, and $R^4$:
(a) all methyl
(b) $R^1$ and $R^3$ both hydrogen; $R^2$ and $R^4$ both methyl
(c) $R^1$ and $R^3$ both hydrogen; $R^2$ methyl, $R^4$ ethyl
(d) $R^1$ and $R^3$ both methyl; $R^2$ methyl, $R^4$ ethyl.

For $R^5$
(a) nitro
(b) chloro
(c) methyl
(d) $CF_3$

For $R^6$
(a) fluoro, chloro or bromo or $S(0)_n R^{12}$
(b) fluoro, chloro or bromo For n' 0 or 2

For $R^{12}$
(a) $C_{1-4}$alkyl
(b) methyl or ethyl

For $R^8$
(a) hydrogen, methyl, $C_{4-8}$alkylcarbonyl or benzoyl
(b) hydrogen

Combinations of these preferred meanings are particularly interesting. The compounds of the present invention of formula I are new substances which can be prepared by methods analogous to methods known in the art, such as those described in European Patent Application EP 186,117 and references cited therein. More particularly, they can be obtained by, for example: reacting an enol ester of formula (II)

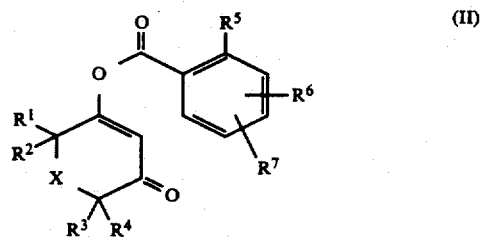

wherein X and $R^1$-$R^7$ are as defined above, with a cyanide source and a moderate base to give a compound of formula I where $R^8$ is hydrogen.

The above reaction is carried out in the presence of a catalytic amount of a source of cyanide anion and/or hydrogen cyanide, together with a molar excess, with respect to the enol ester, of a moderate base. The reaction is conveniently carried out in a solvent which is inert under the reaction conditions, e.g. 1,2.dichloroethane, toluene, acetonitrile, methylene chloride, ethyl acetate, dimethylformamide (DMF) and methyl isobutyl ketone (MIBK). In general, depending on the nature of the reactants and the cyanide source, the rearrangement may be conducted at temperatures up to about 80 C. In some cases, for instance when there is a possible problem of excessive by product formation, the temperatures should be kept at about 40.C maximum.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of $C_2$-$C_5$ aliphatic aldehydes such as acetaldehyde, propionaldehyde, etc., cyanohydrins; zinc cyanide; tri(-lower alkyl) silyl cyanides, notably trimethyl silyl cyanide; and hydrogen cyanide itself. Among cyanohydrins the preferred cyanide source is acetone cyanohydrin. The cyanide source is used in an amount up to about 50 mole percent based on the enol ester. Generally about 1-10 mole % of the cyanide source is preferred.

By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this reaction include both organic bases such as tertiary amines and inorganic bases such as alkali metal carbonates and phosphates. Suitable tertiary amines include trialkylamines such as triethylamine, trialkanolamines such as tri. ethanolamine, and pyridine. Suitable inorganic bases include potassium carbonate and trisodium phosphate. The base is used in an amount of from about 1 to about 4 moles per mole of enol ester, preferably about 1.3-2 moles per mole.

When the cyanide source is an alkali metal cyanide, particularly potassium cyanide, a phase transfer catalyst may be included in the reaction. Particularly suitable phase transfer catalysts are the Crown ethers.

Compounds of formula I where $R^8$ is other than hydrogen can be prepared by reacting a compound of formula Ia

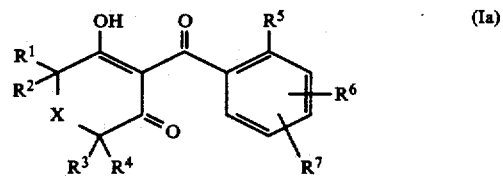

wherein $R^8$-H and $R^1$-$R^7$ are as defined above, with either
(a) the group $R^8$-OH and a catalyst, or
(b) the group $R^8$-Q and a moderate base, wherein Q is a halogen atom,
to give a compound of formula I where $R^8$ is as defined above other than hydrogen.

The above reaction (a) is carried out in the presence of a catalyst such as concentrated sulfuric acid. The reaction is conveniently carried out in a solvent which is also the reactant such as methanol, and at an elevated temperature.

The above reaction (b) is carried out in the presence of a moderate base such as triethylamine or pyridine and conveniently at RT or below.

The compounds of formula I may be recovered from the reaction mixture in which they are formed by working up by established procedures.

The starting materials and reagents employed in the process described herein are either known or, insofar as they are not known, may be produced in a manner analogous to the processes described herein or to known processes.

The compounds of this invention wherein $R^8$-H can have the following four structural formulae because of tautomerism:

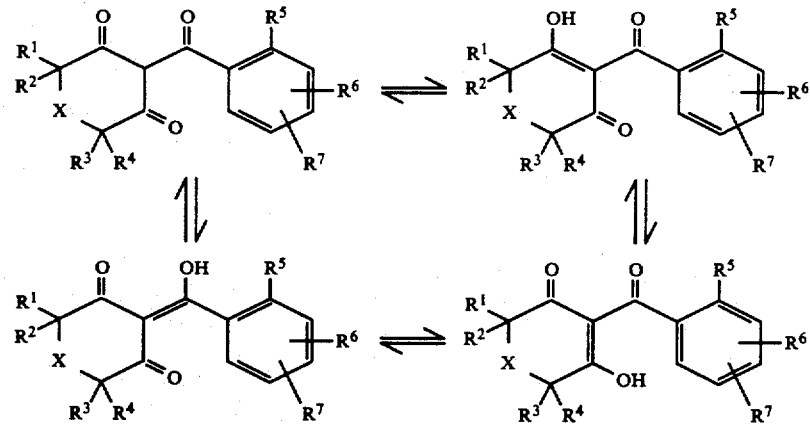

The novel compounds of formula (A) are useful for the control of weeds, using pre. and/or post-emergent treatments. They are also useful as plant growth regulators. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, eg from one-half or less, usually from about one-tenth or less to ten pounds per acre. The application of a compound of the present invention to the "locus" of the weed includes application to the seeds, the plant (weed) or parts of the plant, or the soil.

The term "herbicide," as used herein, refers to an active ingredient which modifies the growth of plants because of phytotoxic or plant growth regulating properties so as to retard the growth of the plant or damage the plant sufficiently to kill it.

The compounds of the present invention, when applied as either post or pre-emergents, demonstrate high levels of herbicidal activity on broadleaf, grass and sedge weeds.

In the use of the compounds of formula A for combatting weeds, a compound of formula A, or mixtures thereof, can conveniently be employed as herbicidal compositions in association with acceptable diluent(s) for application to the weed or its locus. Such compositions also form part of the present invention.

Methods of preparing herbicidal formulations which can be used with a compound of the present invention are described in the literature along with suitable liquid and solid carriers, such as in U.S. Pat. No. 4,192,669 and 4,163,661, which are incorporated herein by reference. The optimum usage of a compound of the present invention is readily determinable by one of ordinary skill in the art using routine testing such as greenhouse testing and small plot testing.

Suitable formulations contain from 0.01 to 99% by weight of active ingredient, from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 25% by weight of active ingredient. Lower or higher levels of active ingredient can, of course, be present depending on the intended use, the physical properties of the compound and the mode of application. Concentrate forms of a composition intended to be diluted before use generally contain between 2 and 90%, preferably between 5 and 81% by weight of active ingredient.

Useful formulations of the compounds of formula A include dusts, granules, suspension concentrates, wettable powders, flowables and the like. They are obtained by conventional manner, e.g. by mixing a compound of formula A with the diluent(s) and optionally with other ingredients.

Alternatively, the compounds of formula A may be used in micro-encapsulated form.

The compounds of formula A can be combined with a cyclodextrin to make a cyclodextrin inclusion complex for application to the pest or its locus.

Agriculturally acceptable additives may be employed in the herbicidal compositions to improve the performance of the active ingredient and to reduce foaming, caking and corrosion, for example.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

"Diluent" as used herein means a liquid or solid agriculturally acceptable material used to dilute a concentrated material to a usable or desirable strength For dusts or granules it can be e.g. talc, kaolin or diatomaceous earth, for liquid concentrate forms for example hydrocarbon such as xylene or an alcohol such as is propanol, and for liquid application forms e.g. water diesel oil.

The compositions of this invention can also compri other compounds having biological activity, e.g. cor pounds having similar or complementary herbicid activity for broadspectrum weed control or compoun having antidotal, fungicidal, insecticidal or insect a tractant activity.

The following examples are provided to illustrate th practice of the present invention. Temperature is giv in degrees Centigrade. RT means room temperature Parts and percentages are by weight.

Preparation of Final Compounds

EXAMPLE 1

2,2-Dimethyl-4-(4-chloro-2-nitrobenzoyl)-2H-thiopy ran-3,5-(4H,6H)-dione

A mixture of 2,2-dimethyl-5-(4-chloro-2-nitrobe zoyloxy)-3,6-dihydro-2H-thiopyran-3-one (8.3 g, 2 mmol), triethylamine (6.8 ml, 48.7 mmol) and aceto cyanohydrin (0.5 ml) in 35 ml of acetonitrile is stirred RT for 16 hours. The reaction mixture is concentrat and taken up in ether. The ether extracts are wash with dilute HCl and with brine, dried and evaporated dryness. The crude product is purified to give 2-2-din thyl.4.(4.chloro.2.nitrobenzoyl).2H-thiopyran-3,5-(4H,6H)-dione (compound 1, Table A).

EXAMPLE 2

2,2,6,6-Tetramethyl-4-(4-chloro-2-nitrobenzoyl)-2H pyran.3,5-(4H,6H)-dione

To a mixture of 2,2,6,6.tetramethyl.5.(4.chloro.2. trobenzoyloxy)-3,6-dihydro-2H-pyran-3-one (5.97 16.9 mmol) and triethylamine (4,70 ml, 33.8 mmol) in ml of acetonitrile is added acetone cyanohydrin ( ml), and the mixture is stirred at RT for 24 hours. T reaction mixture is diluted with ether and extract with aqueous 5% $K_2CO_3$. The aqueous layer is ma acidic with conc. HCl and extracted with ether. T combined organic layers are dried and evaporated give light yellow crystals, which are purified to yi 2,2,6,6.tetramethyl-4-(4-chloro-2-nitrobenzoyl) -2 pyran-3,5-(4H,6H)-dione (compound 8, Table A).

EXAMPLE 3

N-methyl-4-(2,4-dichlorobenzoyl)piperidine-3,5-dio

To a mixture of 5-(2,4-dichlorobenzoyloxy)-1-me yl-1,6-dihydro-3(2H)-pyridone (2.0 g, 6.7 mmol) a triethylamine (1.35 g, 1.9 ml, 13.3 mm©l) in 30 ml acetonitrile is added acetone cyanohydrin (0.05 g, 0 ml, 0.67 mmol). After approx. 30 min., the acetonitril removed and the reaction mixture is diluted in metl lene chloride, washed with dil. HCl and with bri dried and evaporated to dryness to give, followi purification, N-methyl.4.(2,4.dichlorobenzoyl).pip dine.3,5.dione (compound 22, Table A).

EXAMPLE 4

Following the procedures of Examples 1, 2 or 3, each of the compounds under Table A is prepared from the corresponding benzoyl enol ester, triethylamine and acetone cyanohydrin

EXAMPLE 5

2,2,6,6-Tetramethyl.4.(4.chloro-2-nitrobenzoyl).5.methoxy-3,6-dihydro.2H-pyran-3-one A solution of 2,2,6,6.tetramethyl.4.(4.chloro.2.nitrobenzoyl). 2H-pyran.3,5.(4H,6H).dione (0.90 g, 2.54 mmol) and 2 drops of conc. sulfuric acid in 20 ml of methanol is heated under reflux for 48 hours The reaction mixture is concentrated and the residue is taken up in ether. The ethereal solution is washed with aqueous sodium bicarbonate and with brine, dried and evaporated to dryness to give 2,2,6,6.tetramethyl-4-(4-chloro-b 2-nitrobenzoyl)-5-methoxy- 3,6-dihydro.2H-pyran-3-one (compound 65).

EXAMPLE 6

2,2,6,6-Tetramethyl-4-(4.chloro.2.nitro-benzoyl).-5.acetoxy-3,6-dihydro.2H-pyran.3.one To a mixture of 2,2,6,6.tetramethyl.4.(4.chloro.2.nitrobenzoyl).2H-pyran-3,5-(4H,6H)-dione (0.80 g, 2.26 mmol) in methylene chloride (10 ml) containing triethylamine (0.47 ml, 3.39 mmol) is added dropwise at 0'a solution of acetyl chloride (0.27 g, 3.39 mmol) in 5 ml of methylene chloride. The resulting mixture is stirred for 30 min., and is then diluted with methylene chloride, washed, dried and evaporated to dryness to give 2,2,6,6.tetramethyl.4.(4.chloro.2.nitro-benzoyl).-5.acetoxy.3,6-dihydro-2H-pyran-3-one (

EXAMPLE 7

Following the procedures of Example 6, the final compounds under column I are prepared by the reaction of 2,2,6,6.tetramethyl.4.(4.chloro-2-nitrobenzoyl)-2H-pyran-3, 5-(4H, 6H)-dione with the corresponding acyl chlroide.

I 67. 2,2,6,6.tetramethyl.4.(4.chloro.2.nitrobenzoyl).5-propionylo xy-3,6-dihydro.2H-pyran-3-one, an oil
68. 2,2,6,6.tetramethyl.4.(4.chloro.2.nitrobenzoyl).-5.isobutyryl oxy-3,6-dihydro-2H-pyran-3-one, an oil
69- 2,2,6,6-tetramethyl-4-(4-chloro-2-nitrobenzoyl)-5-l piva. loyloxy-3,6-dihydro-2H-pyran-3-one, m.p. 79-
70- 2,2,6,6-tetramethyl-4-(4-chloro-2-nitrobenzoyl) 5-benzoyloxy-3, 6-dihydro-2H-pyran-3-one, m.p. 109°.

EXAMPLE 8

2,6-Dimethyl-2-carbethoxy-4.(4.chloro.2.nitrobenzoyl).2H-pyran-3,5-dione

A mixture of 2,6-dimethyl-2-carbethoxy-5-(4-chloro.2.nitro. benzoyoxy).3,6.dihydro.2H-pyran-3-one (3.5 g, 8.8 mmol), triethylamine (2.5 ml, 17.6 mmol) and acetone cyanohydrin (0.5 ml) is stirred at RT overnight. The reaction mixture is concentrated, and the residue is dissolved in ether and extracted. The combined organic extracts are washed with dil. HCl and with brine, dried and evaporated. The crude product is purified by chromatography to give 2,6.dimethyl.2.carbethoxy-4-(4 chloro-2-nitrobenzoyl)-2H-pyran-3,5-dione.

Composition Examples

EXAMPLE 9

| A. Suspension Concentrate | 20% | 50% |
|---|---|---|
| cpd. 8 | 20.00 | 50.00 |
| distilled water | 63.83 | 34.71 |
| propylene glycol | 8.55 | 6.55 |
| sodium sulfonate of naphthalone-formaldehyde condensate | 6.82 | 7.82 |
| colloidal Mg Al silicate | 0.50 | 0.25 |
| xanthan gum | 0.27 | 0.14 |
| acetylonic glycol blend in propylene glycol (SURFYNOL/TG5) | 0.03 | 0.03 |

The above components are mixed and wet-milled to 514 10 micron particle size.

| B. Wettable Powder - 50% | |
|---|---|
| cpd. 15 | 50.00 |
| sodium sulfonate of naphthalone-formaldehyde condensate | 5.00 |
| kaolinite | 38.00 |
| precipitated silica (amorphous) | 5.00 |
| canionic blend (MORWET/EFW) | 2.00 |

The above components are mixed and wet-milled. The resulting mixture is added to water for spraying.

Biological Activity

EXAMPLE 10

Pre-emergent herbicidal activity of selected compounds of the present invention was determined as follows: Seeds of selected weeds were planted and the soil wad drenched with a solution of water (17%), surfactant (0.17%) and the test compound at a rate equivalent to 1 kg/hectare. Scoring was made two weeks after treatment. The grasses (GR) green foxtail, watergrass, shattercane and wild oats and the broadleafs (BL) annual morning glory, mustard, nightshade and velvetleaf were treated. The average pre-emergent activity of the compounds is presented in Table B below.

EXAMPLE 11

Post-emergent herbicidal activity of selected compounds of the present invention was tested as follows: Seedlings of selected weeds were sprayed with a solution of water/acetone (1:1), surfactant (0.5%) and the test compound at a rate equivalent to 1 kg/hectare. Scoring was made two weeks after spraying. The grasses (GR) green foxtail, watergrass, shattercane and wild oats and the broadleafs (BL) annual morning glory, mustard, soybean and velvetleaf were treated. The average post-emergent activity of the compounds is presented in Table B below.

TABLE A

| Cpd. | X | R¹ | R² | R³ | R⁴ | R⁵ | R⁶ | R⁷ | m.p. (°C) |
|---|---|---|---|---|---|---|---|---|---|
| 1 | S | H | H | CH$_3$ | CH$_3$ | NO$_2$ | 4-Cl | H | oil |
| 2 | S | H | H | H | CH$_3$ | NO$_2$ | 4-Cl | H | 98 |
| 3 | S | H | CH$_3$ | CH$_3$ | CH$_3$ | NO$_2$ | 4-Cl | H | 52 |
| 4 | S | CH$_3$ | CH$_3$ | CH$_3$ | CH$_3$ | NO$_2$ | 4-Cl | H | 52 |
| 5 | O | H | H | H | CH$_3$ | NO$_2$ | 4-Cl | H | 86 |
| 6 | O | H | H | CH$_3$ | CH$_3$ | NO$_2$ | 4-Cl | H | 104 |
| 7 | O | H | CH$_3$ | CH$_3$ | CH$_3$ | NO$_2$ | 4-Cl | H | oil |
| 8 | O | CH$_3$ | CH$_3$ | CH$_3$ | CH$_3$ | NO$_2$ | 4-Cl | H | 87 |
| 9 | O | CH$_3$ | CH$_2$CH$_3$ | CH$_3$ | CH$_2$CH$_3$ | NO$_2$ | 4-Cl | H | 67 |
| 10 | O | CH$_3$ | CH$_3$ | CH$_3$ | CH$_3$ | Cl | 4-Cl | H | oil |
| 11 | O | CH$_3$ | CH$_3$ | CH$_3$ | CH$_3$ | Cl | 4-Br | H | |
| 12 | O | CH$_3$ | CH$_3$ | CH$_3$ | CH$_3$ | Cl | 4-NO$_2$ | H | 128 |
| 13 | O | CH$_3$ | CH$_3$ | CH$_3$ | CH$_3$ | Cl | 4-SO$_2$CH$_3$ | H | 140 |
| 14 | O | CH$_3$ | CH$_3$ | CH$_3$ | CH$_3$ | NO$_2$ | 4-CF$_3$ | H | |
| 15 | O | CH$_3$ | H | CH$_3$ | H | NO$_2$ | 4-Cl | H | 121 |
| 16 | O | H | H | H | H | NO$_2$ | 4-Cl | H | 164 |
| 17 | O | CH$_3$ | CH$_3$ | CH$_3$ | CH$_3$ | NO$_2$ | H | H | 128 |
| 18 | O | CH$_3$ | CH$_3$ | CH$_3$ | CH$_3$ | SO$_2$CH$_3$ | 4-Cl | H | |
| 19 | S | H | CH$_3$ | CH$_3$ | CH$_3$ | Cl | 4-Cl | H | 100 |
| 20 | S | CH$_3$ | CH$_3$ | CH$_3$ | CH$_3$ | Cl | 4-Cl | H | 67.5 |
| 21 | S | CH$_3$ | CH$_3$ | CH$_3$ | CH$_3$ | Cl | 4-Br | H | 81.5 |
| 22 | NCH$_3$ | H | H | H | H | Cl | 4-Cl | H | |
| 23 | O | CH$_3$ | CH$_2$CH$_3$ | CH$_3$ | CH$_3$ | NO$_2$ | 4-Cl | H | 82 |
| 24 | O | CH$_3$ | CH$_3$ | CH$_3$ | CH$_3$ | NO$_2$ | 4-Br | H | 90 |
| 25 | O | CH$_3$ | CH$_3$ | CH$_3$ | CH$_3$ | NO$_2$ | 4-F | H | 95 |
| 26 | O | CH$_3$ | CH$_3$ | CH$_3$ | CH$_3$ | CF$_3$ | H | H | oil |
| 27 | O | CH$_3$ | CH$_3$ | CH$_3$ | CH$_3$ | Cl | 4-F | H | 70 |
| 28 | O | CH$_3$ | CH$_3$ | CH$_3$ | CH$_3$ | F | 4-Cl | H | 223 |
| 29 | O | CH$_3$ | CH$_3$ | CH$_3$ | CH$_3$ | NO$_2$ | 3-Cl | H | 130 |
| 30 | O | CH$_3$ | CH$_3$ | CH$_3$ | CH$_3$ | NO$_2$ | 3-CH$_3$ | H | 162 |
| 31 | O | H | CH$_2$CH$_3$ | H | H | NO$_2$ | 4-Cl | H | oil |
| 32 | O | H | CH$_2$CH$_3$ | H | CH$_3$ | NO$_2$ | 4-Cl | H | 97 |
| 33 | O | H | CH$_2$CH$_3$ | H | CH$_3$ | NO$_2$ | 4-Br | H | 111 |
| 34 | O | CH$_3$ | CH$_2$CH$_3$ | H | H | NO$_2$ | 4-Cl | H | 102 |
| 35 | O | CH$_3$ | CH$_2$CH$_3$ | H | CH$_3$ | NO$_2$ | 4-Cl | H | oil |
| 36 | O | CH$_3$ | H | H | CH$_2$CH$_3$ | CF$_3$ | 4-F | H | 61 |
| 37 | O | CH$_3$ | CH$_3$ | H | H | NO$_2$ | 4-F | H | oil |
| 38 | O | CH$_3$ | CH$_3$ | CH$_3$ | CH$_3$ | NO$_2$ | 4-SO$_2$CH$_3$ | H | 151 |
| 39 | O | CH$_3$ | CH$_3$ | H | H | NO$_2$ | 4-SO$_2$CH$_3$ | H | oil |
| 40 | O | H | CH$_3$ | H | CH$_3$ | NO$_2$ | 4-SO$_2$CH$_3$ | H | 140–143 |
| 41 | O | H | CH$_2$CH$_3$ | H | CH$_3$ | NO$_2$ | 4-SO$_2$CH$_3$ | H | oil |
| 42 | O | H | CH$_2$CH$_3$ | H | CH$_3$ | Cl | 4-SO$_2$CH$_3$ | H | oil |
| 43 | O | H | H | CH$_3$ | CH$_3$ | Cl | 4-SO$_2$CH$_3$ | H | oil |
| 44 | O | CH$_3$ | CH$_3$ | CH$_3$ | CH$_3$ | Cl | 4-SO$_2$CH$_3$ | 3-Cl | 64.5 |
| 45 | O | H | CH$_3$ | H | CH$_3$ | Cl | 4-Cl | 3-Cl | oil |
| 46 | O | H | CH$_2$CH$_2$CH$_3$ | H | CH$_3$ | NO$_2$ | 4-Cl | H | oil |
| 47 | O | —CH$_2$—CH$_2$—CH$_2$—CH$_2$— | | H | H | NO$_2$ | 4-Cl | H | oil |
| 48 | O | H | CH$_2$CH$_3$ | CH$_3$ | CH$_3$ | NO$_2$ | 4-Cl | H | oil |
| 49 | O | H | CH$_2$CH$_3$ | H | CH$_2$CH$_3$ | NO$_2$ | 4-Cl | H | 83 |
| 50 | O | H | CH$_3$ | H | CH$_2$CH$_3$ | NO$_2$ | 4-H | H | 105 |
| 51 | O | CH$_3$ | CH$_3$ | CH$_3$ | CH$_3$ | NO$_2$ | 4-CH$_3$ | H | 93 |
| 52 | O | CH$_3$ | CH$_3$ | CH$_3$ | CH$_3$ | CH$_3$ | 4-Br | H | oil |
| 53 | O | CH$_3$ | CH$_3$ | CH$_3$ | CH$_3$ | CF$_3$ | 4-F | H | oil |
| 54 | O | CH$_3$ | H | CH$_2$CH$_3$ | H | NO$_2$ | 4-F | H | oil |
| 55 | O | CH$_3$ | H | CH$_2$CH$_3$ | H | NO$_2$ | 4-SCH$_3$ | H | 103 |
| 56 | O | CH$_3$ | H | CH$_2$CH$_3$ | H | NO$_2$ | 4-SCH$_2$CH$_3$ | H | oil |
| 57 | O | CH$_3$ | H | CH$_2$CH$_3$ | H | Cl | 4-SCH$_2$CH$_3$ | H | oil |
| 58 | O | CH$_3$ | H | CH$_3$ | H | Cl | 4-SCH$_2$CH$_3$ | H | oil |
| 59 | O | CH$_3$ | CH$_3$ | CH$_3$ | CH$_3$ | NO$_2$ | 4-SCH$_2$CH$_3$ | H | 48.5 |
| 60 | O | CH$_3$ | CH$_3$ | CH$_3$ | CH$_3$ | NO$_2$ | 4-SCH$_3$ | H | 97.5 |
| 61 | S | CH$_3$ | CH$_3$ | CH$_3$ | CH$_3$ | CF$_3$ | H | H | oil |
| 62 | S | H | H | H | H | NO$_2$ | 4-Cl | H | 172 |
| 63 | NCH$_3$ | H | H | CH$_3$ | CH$_3$ | NO$_2$ | 4-Cl | H | 285 |
| 64 | NCH(CH$_3$)$_2$ | H | CH$_3$ | H | CH$_3$ | NO$_2$ | 4-Cl | H | 190 |
| 71 | O | H | CH(CH$_3$)$_2$ | H | CH$_3$ | NO$_2$ | 4-Cl | H | oil |
| 72 | O | CH$_3$ | CH$_3$ | CH$_3$ | CH$_3$ | Cl | 4-Cl | 3-Cl | 78 |
| 73 | O | CH$_3$ | CH$_3$ | CH$_3$ | CH$_3$ | Cl | 4-OCH$_3$ | 3-Cl | 77 |

TABLE B

| | % Herbicidal Activity of 1kg/hectare | | | |
|---|---|---|---|---|
| | PRE | | POST | |
| Cpd | GR | BL | GR | BL |
| 7 | 100 | 100 | 98 | 90 |
| 8 | 100 | 95 | 100 | 100 |
| 10 | 100 | 100 | 95 | 82 |
| 15 | 97 | 98 | 97 | 100 |
| 17 | 100 | 87 | 100 | 97 |
| 23 | 100 | 87 | 97 | 100 |
| 24 | 100 | 98 | 100 | 97 |
| 25 | 100 | 100 | 100 | 100 |
| 26 | 56 | 42 | 95 | 81 |
| 27 | 92 | 95 | 95 | 82 |
| 32 | 98 | 100 | 78 | 93 |
| 33 | 100 | 100 | 96 | 100 |
| 38 | 78 | 78 | 100 | 100 |
| 40 | 89 | 100 | 55 | 100 |
| 41 | 97 | 100 | 67 | 100 |
| 42 | 82 | 97 | 87 | 100 |
| 44 | 100 | 100 | 100 | 100 |
| 45 | 95 | 100 | 95 | 100 |
| 48 | 100 | 100 | 98 | 97 |
| 49 | 98 | 97 | 98 | 100 |
| 50 | 100 | 100 | 97 | 100 |
| 51 | 60 | 100 | 78 | 100 |
| 52 | 100 | 100 | 100 | 100 |
| 53 | 88 | 75 | 97 | 100 |
| 54 | 100 | 100 | 100 | 100 |
| 55 | 100 | 100 | 100 | 100 |
| 60 | 100 | 100 | 100 | 100 |
| 68 | 100 | 100 | 100 | 100 |
| 69 | 100 | 100 | 100 | 100 |
| 70 | 100 | 100 | 100 | 100 |
| 71 | 100 | 100 | 95 | 100 |
| 72 | 100 | 100 | 72 | 87 |
| 73 | 73 | 76 | 100 | 100 |
| 74 | 73 | 67 | 93 | 90 |

The starting compounds of formula II herein are known or, in cases where they are novel, can be produced by methods analogous to known methods or by methods described herein. Thus, the enol esters of formula II can be prepared by the reaction of a heterocyclohexane-3,5.dione of formula III (wherein $R^1$–$R^4$ are defined as hereinabove) with a benzoyl halide of formula IV (wherein Q is a halogen atom and $R^5$–$R^7$ are as defined hereinabove) in the presence of a moderate base such as triethylamine.

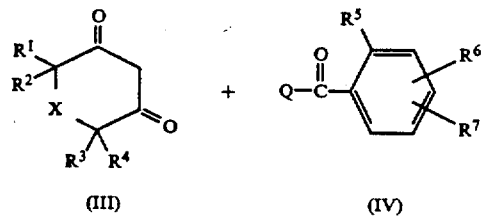

2H-Pyran-3,5-(4H,6H)-diones of formula III (where X is oxygen) can be synthesized by methods such as (a) described by Morgan et al., *JACS* 79:422 (1957), or (b) by treating a 2,5 substituted furanidine.3,4.dione - (from Korobitsyna et al., *J. Gen. Cheml USSR* 27:1859 (1957)) with an alkyl diazoacetate, followed by heating in the presence of water. The 2H-thiopyran.3,5.(4H,6H).diones and piperidine of formula III (where X is sulfur or $NR^{11}$) can be synthesized by reacting a sulfide or sarcosinate of formula V (alk=methyl or ethyl and $X^1$=S or $NR^{11}$) with sodium methoxide.

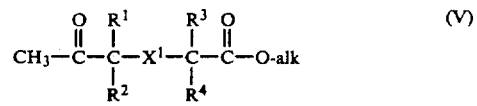

Intermediate Compounds

The following examples are presented to illustrate representative methods of preparing the intermediate compounds.

EXAMPLE 12

2,2,6,6-Tetramethyl.2H-pyran-3,5.(4H,6H).dione

Boron trifluoride etherate (4.8 ml, 39.0 mmol) is added to a solution of 2,2,5,5-tetramethyl-furanidine.3,4.dione (15.0 g, 78.0 mmol) in 20 ml of anhydrous ether. Ethyl diazoacetate (12.3 ml, 117.0 mmol) in 20 ml of ethyl ether is added at a rate such that nitrogen evolution does not become vigorous. The mixture is stirred at RT for 12 hours and is then quenched with water. The mixture is diluted with ether and washed with brine, then extracted with 5% $K_2CO_3$. The $K_2CO_3$ solution is washed with ether and neutralized with conc. HCl. The product is extracted with ether, dried and evaporated to give 4.carbethoxy.2,2,6,6.tetramethyl-2H-pyran-3,5-(4H, 6H).dione, a pink oil.

The above trione (5.11 g, 21.1 mmol) is dissolved in 25 ml of dimethyl sulfoxide, and water is added (0.8 ml, 42.2 mmol). The mixture is heated at 120 for 1 hour, or until gas evolution has ended. The reaction mixture is diluted with ether and washed with sat. NaCl. The solvent is removed and the crude product triturated with ether/hexane to give 2,2,6,6.tetramethyl.2H-pyran.3,5.(4H,6H).dione, as white crystals.

EXAMPLE 13

2,2,6,6.Tetrassethyl.5.(4.chloro.2.nitrobenzoyloxy)-3,6-dihydro.2H-pyran.3.one

A mixture of 2,2,6,6.tetramethyl.2H-pyran-3,5.(4H,6H) dione (3.59 g, 21.1 mmol) and 4.chloro.2.nitrobenzoyl chloride (4.63 g, 21.1 mmol) in 0 ml of methylene chloride is cooled to 0, after which triethylamine (2.94 ml, 27.4 mmol) is added dropwise. The mixture is stirred at RT for hour, then is taken up in methylene chloride and washed with water and with brine. The solvent is evaporated off to give crystalline 2,2,6,6-tetramethyl-5-(4-chloro-2-nitrobenzoyloxy)-3, 6-dihydro-2H-pyran-3-one.

EXAMPLE 14

2,2.Dimethyl-2H-thiopyran-3,5.(4H,6H) dione

Sodium metal (2.03 g) is dissolved in methanol (25 ml) and the methanol is removed by distillation to give sodium methoxide, which is dried under vacuum and then suspended in 50 ml of benzene. Ethyl acetonylmercaptoisobutyrate (17.89 g, 87.6 mmol) is added dropwise to the suspension, and the mixture is stirred at RT for 2 hours. The reaction mixture is extracted with water, and the benzene layer is discarded. The aqueous layer is washed with ether, neutralized with conc. HCl and extracted with ether The combined ether extracts are dried, evaporated to dryness and purified to give 2,2.dimethyl.2H-thiopyran.3,5.(4H,6H)-dione.

EXAMPLE 15

2,2-Dimethyl-5-(4.chloro.2.nitrobenzoyloxy)-3,6-dihydro-2H-thiopyran-3-one

Following the procedure of Example 7, 2,2.dimethyl.2H-thiopyran. 3,5.(4H,6H).dione (4.0 g, 25.3 mmol) and 4.chloro.2.nitrobenzoyl chloride (5.56 g, 25.3 mmol) are reacted together to give 2,2.dimethyl.5.(4-chloro-2-nitrobenzoyloxy)-3, 6-dihydro-2-H-thiopyran-3-one, a slightly brownish oil.

EXAMPLE 16

Sodium salt of 1.methyl.1,6.dihydro.3(2H).pyridone

Sodium methoxide, prepared as in Example 9 from sodium metal (0.87 g, 38.0 mmol) and methanol (10 ml), is suspended in 30 ml of benzene and chilled while methyl N-acetonyl sarcosinate (6.0 g, 38.0 mmol) is added dropwise. The mixture is stirred for 1.5 hours, after which the benzene is removed to give the sodium salt of 1.methyl.1,6.dihydro.3(2H)-pyridone.

EXAMPLE 17

5-(2,4.Dichlorobenzoyloxy).1.methyl.1,6.dihydro-3(2)-pyridone

The sodium salt of 1-methyl-1,6-dihydro.3.(2H).pyridone from Example 11 is suspended in 25 ml of 1,2.dichloroethane and chilled. 2,4.Dichlorobenzoyl chloride (8.0 g, 5.3 ml, 38.0 mmol) in 5 ml of dichloroethane is added dropwise, and the mixture is stirred at RT for 2 hours. The solvent is removed, and the residue is taken up in methylene chloride, washed with water and with brine, dried and evaporated to dryness to give, after purification, 5.(2,4.dichlorobenzoyloxy)-1-methyl-1,6-dihydro-3(2H)-pyridone.

EXAMPLE 18

2,6.Dimethyl.2.carbethoxy-2H-pyran.3,5.dione

Mercuric oxide (0.5 g) is added to a 50% sulfuric acid solution (2 ml), and the mixture is heated to 80 until white mercuric sulfate and visible. Water (5 ml) and ethanol (20 ml) are added and the mixture is heated to reflux. Diethyl 2.[2.(3.butynyloxy)].2.methylmalonate (30.0 g, 124.0 mmol) is added dropwise to the mixture under reflux, and the mixture is stirred overnight. The ethanol is then removed under vacuum and the residue is dissolved in ether, then washed with brine, dried and evaporated. The crude product is purified by chromatography to give diethyl 2.[2.(3.oxobutyloxy)].2.methylmalonate.

Diethyl 2.[2.(3.oxobutyloxy)].2.methylmalonate (20.0 g, 76.8 mmol) is added dropwise to a suspension of sodium methoxide [prepared from 1.77 g (76.8 mmol) of sodium metal and 25 ml of methanol]in benzene (50 ml), and the mixture is stirred overnight. The reaction mixture is extracted with water, and the aqueous layer washed with ether, neutralized with conc. HCl, and extracted again with ether. The extract is dried and evaporated to give 2,6.dimethyl.2.carbethoxy.2H-pyran.3,5.dione.

EXAMPLE 19

2,6-Dimethyl-2-carbethoxy-5-(4-chloro-2-nitro-benzoyloxy)-3,6-dihydro-2H-pyran-3-one A mixture of 2,6.dimethyl.2.carbethoxy.2H-pyran-3,5-dione (2.0 g, 9.3 mmol) and 4.chloro.2.nitrobenzoyl chloride (2.05 g, 9.3 mmol) in 50 ml of methylene chloride is cooled to 0., after which triethylamine (1.69 ml, 12.1 mmol) is added dropwise. The mixture is stirred at RT for 1 hour, after which it is diluted with methylene chloride and washed with water and with brine. The crude product is dried and evaporated to give a mixture of 2, 6-dimethyl-2-carbethoxy-5-(4-chloro-2-nitrobenzoyloxy)-3,6-dihydro-2H-pyran-3-one and 2,6-dimethyl-2-carbethoxy-3-(4-chloro-2nitrobenzoyloxy)-3,6-dihydro-2H-pyran-5-one.

What is claimed is:

1. A compound of formula I wherein $R^1$ and $R^3$ are both methyl or both hydrogen;

$R^2$ and $R^4$ are both methyl;

$R^5$ is nitro and $R^6$ is fluoro, chloro, bromo or $SR^{12}$;

$R^{12}$ is $C_{1-4}$alkyl; and $R^8$ is hydrogen, methyl, $C_{1-4}$alkylcarbonyl or benzoyl.

2. A compound of formula J according to claim 1 wherein each of $R^1$, $R^2$, $R^3$ and $R^4$ is methyl.

3. A compound of formula J according to claim 1 wherein $R^6$ is fluoro, chloro or bromo.

4. A compound according to claim 1 wherein $R^8$ is hydrogen.

5. A compound according to claim 1 which is 2,2,6,6-tetramethyl-4 (4-chloro-2-nitrobenzoyl)-2H-pyran-3, 5-(4H, 6H)-dione.

6. An herbicidal composition comprising an herbicidally effective amount of a compound of formula I according to claim 1 in association with suitable diluents and additives.

7. A method of controlling weeds which comprises applying to the weeds or their locus an herbicidally effective amount of a compound of formula I according to claim 1.

* * * * *